(12) United States Patent
Maschke

(10) Patent No.: US 8,337,512 B2
(45) Date of Patent: Dec. 25, 2012

(54) DEVICE AND WORKFLOW FOR MINIMALLY-INVASIVE THERAPY, IN PARTICULAR NEEDLE GUIDANCE

(75) Inventor: Michael Maschke, Lonnerstadt (DE)

(73) Assignee: Siemens Aktiengesellschaft, Munich (DE)

( * ) Notice: Subject to any disclaimer, the term of this patent is extended or adjusted under 35 U.S.C. 154(b) by 1014 days.

(21) Appl. No.: 12/329,831

(22) Filed: Dec. 8, 2008

(65) Prior Publication Data

US 2010/0145358 A1    Jun. 10, 2010

(51) Int. Cl.
*A61B 19/00* (2006.01)
(52) U.S. Cl. ....................................................... 606/130
(58) Field of Classification Search .................. 128/922, 128/920, 923, 204.18, 204.21–204.26
See application file for complete search history.

(56) References Cited

U.S. PATENT DOCUMENTS

| | | | |
|---|---|---|---|
| 5,183,038 A * | 2/1993 | Hoffman et al. | 128/204.21 |
| 5,239,994 A | 8/1993 | Atkins | |
| 5,764,723 A | 6/1998 | Weinberger et al. | |
| 5,949,080 A * | 9/1999 | Ueda et al. | 250/492.3 |
| 6,728,396 B2 * | 4/2004 | Wang | 382/129 |
| 6,959,266 B1 * | 10/2005 | Mostafavi | 702/189 |
| 7,599,466 B2 | 10/2009 | Boese et al. | |
| 7,620,146 B2 * | 11/2009 | Mostafavi | 378/62 |
| 2004/0117032 A1 * | 6/2004 | Roth | 623/23.72 |
| 2006/0264762 A1 * | 11/2006 | Starr | 600/483 |
| 2008/0242971 A1 * | 10/2008 | Klingenbeck-Regn | 600/407 |
| 2009/0306547 A1 * | 12/2009 | Iddan et al. | 600/585 |

FOREIGN PATENT DOCUMENTS

DE    102005016472 A1    10/2006

OTHER PUBLICATIONS

Chest—1999 Rajesh G. Patel—116; 1689-1694.
Correspondence—Wrist Actigraphy in Anesthesia—ANESTH 2001 pp. 713-720.
SMI Susquehanna Micro, 2007—Acutronic Monsoon Universal Jet Ventilator, Jet Ventilaiton, Ve.

* cited by examiner

*Primary Examiner* — Loan Thanh
*Assistant Examiner* — Shila Jalalzadeh Abyane
(74) *Attorney, Agent, or Firm* — Schiff Hardin LLP

(57) ABSTRACT

In a method or system for minimally-invasive therapy on a patient, a minimally-invasive therapy apparatus is provided. While performing the minimally-invasive therapy on the patient with a minimally-invasive therapy apparatus, the patient is ventilated with a jet ventilator to reduce a magnitude of the patient's breathing and increase a frequency of the patient's breathing.

23 Claims, 5 Drawing Sheets

US 8,337,512 B2

DEVICE AND WORKFLOW FOR MINIMALLY-INVASIVE THERAPY, IN PARTICULAR NEEDLE GUIDANCE

BACKGROUND

Minimally-invasive medical therapies are increasingly gaining importance. In the treatment of coronary heart disease, the surgical bypass operation on the heart is clearly declined in favor of balloon dilation (PTCA=percutaneous transluminal coronary angioplasty) and the insertion of a stent. In arterial fibrillation, ablation in the atrium has established itself in recent years. Minimally-invasive procedures are also clearly increasing in the fields of biopsies, spinal column therapies and tumor ablation.

Medical imaging that shows the vessels, organs and medical instruments in the organism in real time remains a requirement in all minimally-invasive interventions. Image artifacts thereby arise due to body and organ movement (for example due to breathing). For example, given a lung tumor the tumor moves between 1 and 2 cm during one breathing cycle.

Modern imaging devices such as computer tomographs have what is known as respiration gating; the breathing cycle is thereby taken into account in the image reconstruction, and the radiologist acquires exposures in which the movement artifacts that arise due to breathing have been corrected.

A solution which takes into account the respiratory movement in radiation therapy is known from U.S. Pat. No. 5,764,723, "Apparatus and Method to Gate a Source for Radiation Therapy".

In biopsies or tumor ablation, the therapy needle must still be introduced manually by the physician into the organ area to be treated. For this the patient is required to hold his breath, or the physician attempts to insert the needle while estimating the breathing cycle. This method is very dependent on the cooperation of the patient and the manual/surgical skill of the physician.

The solution described in pending Siemens AG German Patent Application 2008P0365 DE, ("Movement-Controlled, in Particular Breathing-Controlled Needle Guidance"), improves the guidance of rigid instruments in an organism and reduces the requirements for the cooperation readiness of the patient or the skillfulness of the physician. However, one disadvantage is that the respiratory movement of the patient must be correctly detected.

SUMMARY

It is an object to find a solution that permits a safe insertion and guidance of an instrument, independent of the patient and the skill of the physician.

In a method or system for minimally-invasive therapy on a patient, a minimally-invasive therapy apparatus is provided. While performing the minimally-invasive therapy on the patient with the minimally-invasive therapy apparatus, the patient is ventilated with a jet ventilator to reduce a magnitude of the patient's breathing and increase a frequency of the patient's breathing.

DESCRIPTION OF THE PREFERRED EMBODIMENTS

Figure 1:
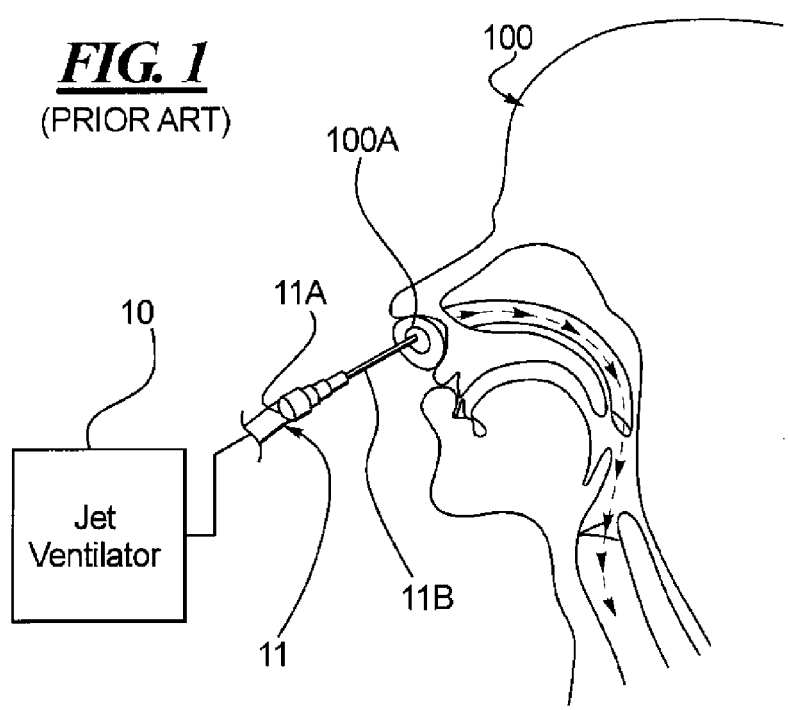
FIG. 1 is a side partial cross-sectional view illustrating a prior art jet ventilator needle injecting pulsating ventilated air into a nose of a patient.

For the purposes of promoting an understanding of the principles of the invention, reference will now be made to preferred embodiments/best mode illustrated in the drawings and specific language will be used to describe the same. It will nevertheless be understood that no limitation of the scope of the invention is thereby intended, and such alterations and further modifications in the illustrated devices and such further applications of the principles of the invention as illustrated as would normally occur to one skilled in the art to which the invention related are included.

According to one preferred embodiment, the patient is respirated with what is known as a jet (high-frequency) ventilator during an intervention (advantageously for a needle insertion and guidance procedure such as into a tumor).

Such a jet ventilator is available from the company http://www.acutronic-medical.ch or http://www.bun1.com/controls.html. U.S. Pat. No. 5,239,994, "Jet Ventilator System", also discloses a jet ventilator. This document is incorporated herein.

Due to the high-frequency respiration (60 to 700 respiration cycles per minute) and reduced magnitude of the respiration, a distinct rising and falling of the ribcage no longer occurs, rather only a high-frequency oscillation of the lungs with very small movement amplitude that barely causes interfering image artifacts.

Two techniques can thereby be used: a) insertion of a respiration tube through the nose (see "Effectiveness of transnasal jet Ventilation—a teaching aid", James R. Boyce); or b) insertion of a respiration tube via the trachea (see "Conventional Methods are Unsuccessful Provide Oxygenation and Ventilation When A Safe, Quick, and Temporary Way To: *Percutaneous Transtracheal Jet Ventilation", Rajesh G. Patel). Technique a) above is preferred.

Particularly advantageous is the integration of this device into an angiographic/cardiological x-ray system comprised of high voltage generator, x-ray radiator(s), radiation diaphragm, image display unit(s), patient table, radiator and detector tripod with a digital image system, in particular a DynaCT and/or DynaCT Card x-ray device (of Siemens AG). A device with which both angiographic x-ray exposures and CT-like images can be re-constructed is disclosed in DE 102005016472 "Operating Method for an X-ray System, Corresponding Operating Method for a Computer and Corresponding Subjects". A gating signal can thereby additionally be derived by the jet ventilator and be taken into account in the image reconstruction. The respiration curve can be displayed at the imaging unit.

The guidance of the instrument (needle) can thereby be implemented by hand by the medical personnel or via a needle guidance robot that does not need to be respiration-controlled due to the low movement amplitude. Alternatively, a signal can additionally be lifted from the jet ventilator in order to further improve the robot control.

For example, the high-frequency respiration can be used by such methods in the following methods or combinations: a) x-ray systems; b) sonography, including IVUS; c) radioscopy (fluoroscopy); d) angiographic and cardiological x-ray systems; e) optical coherence tomography (OCT); f) positron emission tomography (PET); g) SPECT; h) computer tomography; i) nuclear magnetic resonance tomography, including intravascular/intracardial MR; j) optical exposures, including endoscopy; k) fluorescence and optical markers (molecular imaging); and l) radiation therapy or particle therapy A great advantage of the preferred embodiment lies in the avoidance of movements of the ribcage with large amplitude, which cause unwanted organ, tumor and vessel movements during the intervention.

Preferred embodiments will now be described in greater detail with respect to FIGS. 1-7.

FIG. 1 shows a prior art jet ventilator 10 with a ventilator output 11 comprising a hose 11A and needle 11B inserted at a nose 100A of a patient 100.

Figure 2:
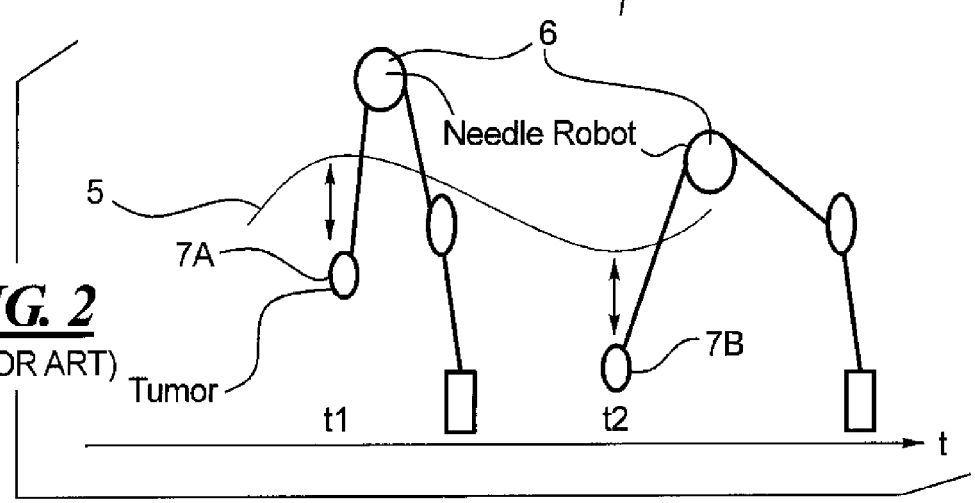
FIG. 2 is a graph showing a normal breathing curve and tumor movement during needle insertion into the tumor without respiration or with conventional respiration according to the prior art.

FIG. 2 shows a known prior art relationship between movement of a tumor 7A, 7B as a result of respiration of a patient having a breathing curve 5 without respiration or with a conventional prior art respirator A needle robot 6 must therefore track the movement of the tumor, which is very disadvantageous as previously indicated.

Figure 3:
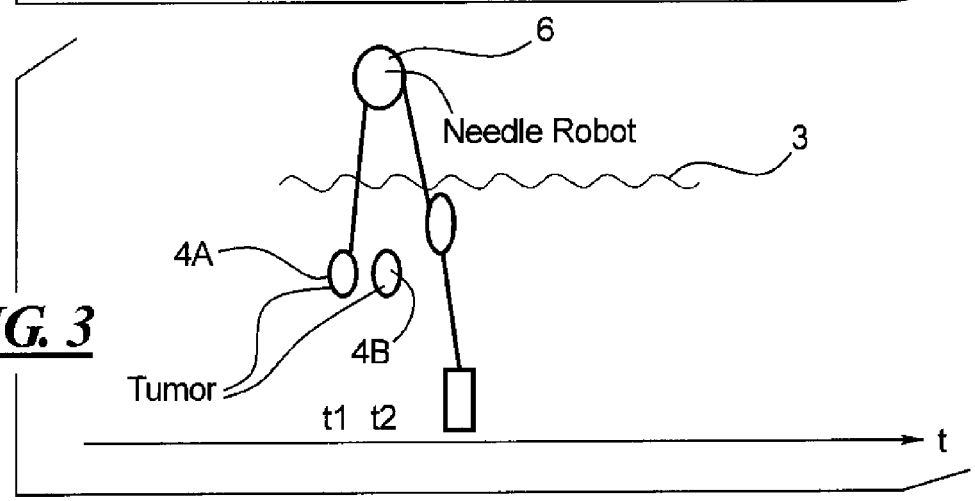
FIG. 3 is a graph showing a breathing curve and tumor movement when a jet ventilation device is employed during needle insertion into a tumor.

FIG. 3 shows a needle robot 6 for injecting a needle into a tumor 4A, 4B which does not move nearly as much as the tumor does in previous FIG. 2 since a jet ventilation is employed so that the patient's breathing curve has much smaller peaks and valleys as indicated at 3. Thus with the preferred embodiment, it is much easier for the needle robot to insert a needle to take a sample from the tumor over a time period corresponding to a plurality of small undulations of the patient's breathing curve 3.

Figure 4:
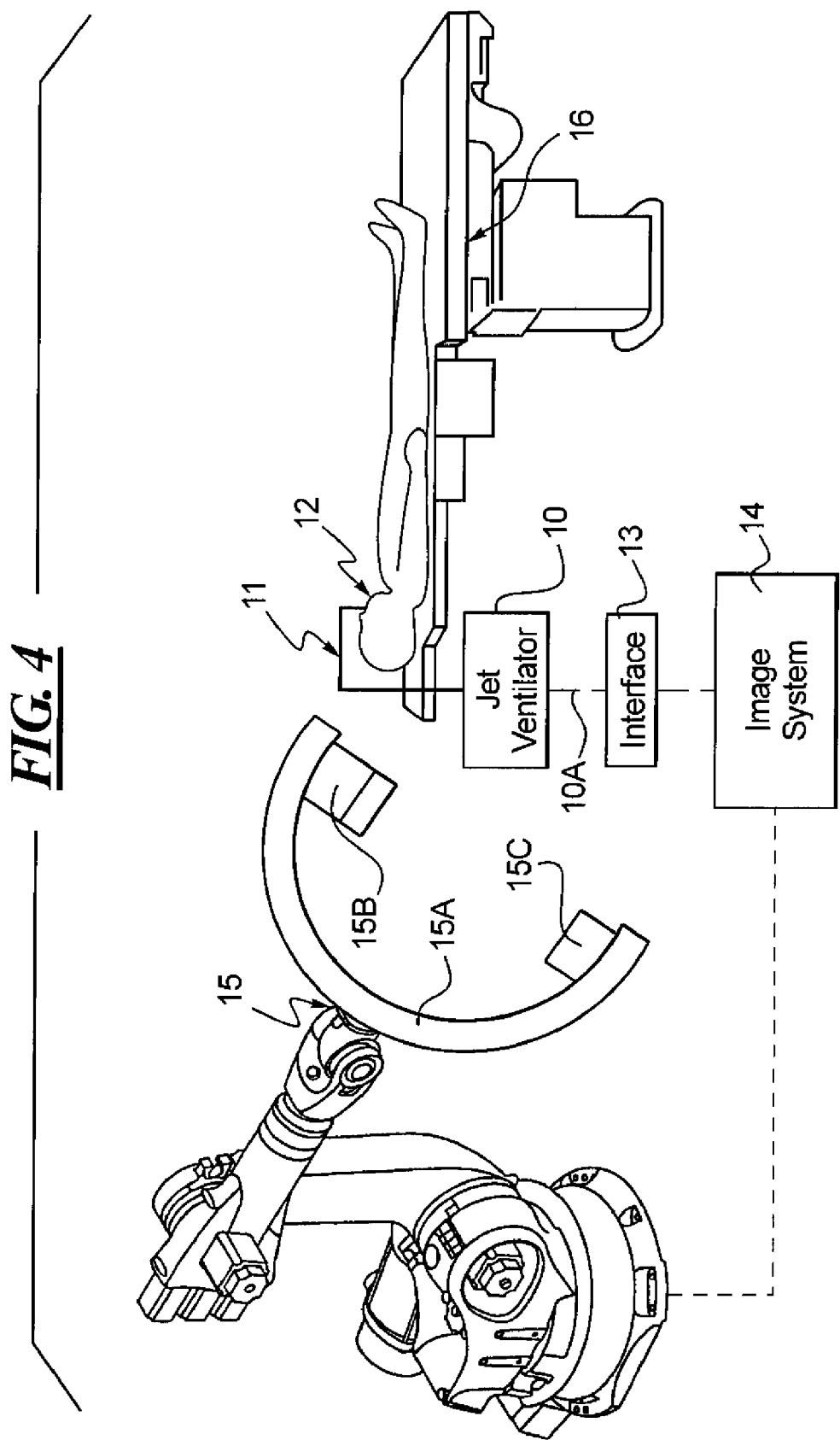
FIG. 4 is a schematic illustration of a jet ventilator being used for a patient to be scanned by a robotic x-ray radiator and detector system with an associated image system connected to the jet ventilator for processing control.

FIG. 4 shows an illustration of a patient 12 respirated, such as by a needle to the patient's nose, via a ventilator output line 11 to a jet ventilator 10. The patient lies on a table 16 for undergoing an x-ray scan by use of a floor-mounted articulated arm robot 15 with a C-shaped arm 15A with x-ray radiator 15B and detector 15C.

The jet ventilator 10 has a signal output time 10A connected via an interface 13 between the jet ventilator 10 and an image system 14 for the x-ray system 15. Thus the ventilator can control the image system to take a count of even small undulations in the patient's breathing curve.

Figure 5:
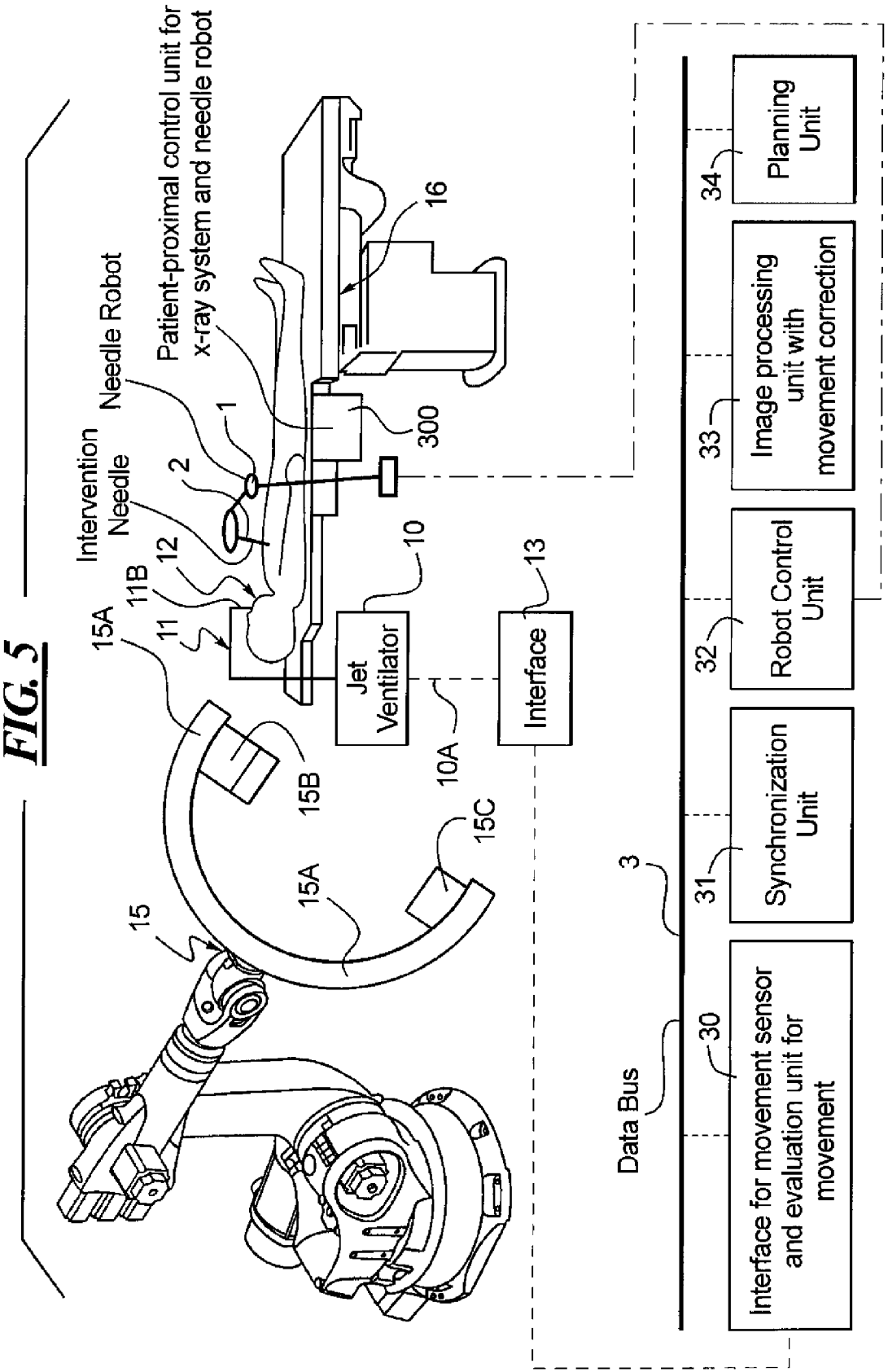
FIG. 5 is a schematic illustration of the patient being respirated with a jet ventilator and undergoing a scan with a robotic x-ray radiation and detector during robotic needle insertion, such as into a tumor, and the use of a data bus for processing control by the use of the jet ventilator with at least one or more system modules.

In FIG. 5 a system is provided with a robot 1 for insertion of an intervention needle 2 with movement compensation. As shown in FIG. 5, the patient 12 may undergo an x-ray radiation scan for needle guidance by the robotic system 15 during the intervention with the needle robot 1 for example to obtain a biopsy from a patient's tumor while the patient 12 is being ventilated by a jet ventilator 10 via ventilator output line 11 and ventilator needle 11B. The x-ray radiator system 15 with x-ray radiator 15B and detector 15C is used to continuously image the procedure to insure proper replacement of the needle into the tumor while the patient is being respirated by the jet ventilator.

In FIG. 5, the jet ventilator 10 connects an output signal line 10A through interface 13 to an interface unit 30 for movement sensor and movement evaluation. Interface 30 is connected to a data bus 3 which also connects to: a synchronization unit 31 for movement deactivation, image correction, and robot control; a robot unit 32; an image processing unit 33 with movement correction; and a planning unit 34 for planning the intervention, and determination of start and target coordinates for guidance of the needle 2 of the needle robot 1. The method with jet-ventilator will also work without a needle robot when the operator uses his hands A patient-proximal control unit 300 for the x-ray system 15 with C-shaped arm 15A and the needle robot 1 is provided for proper placement of the patient 12 on the patient table 16 with respect to the needle robot 1 and the x-ray system 15.

Figure 6:
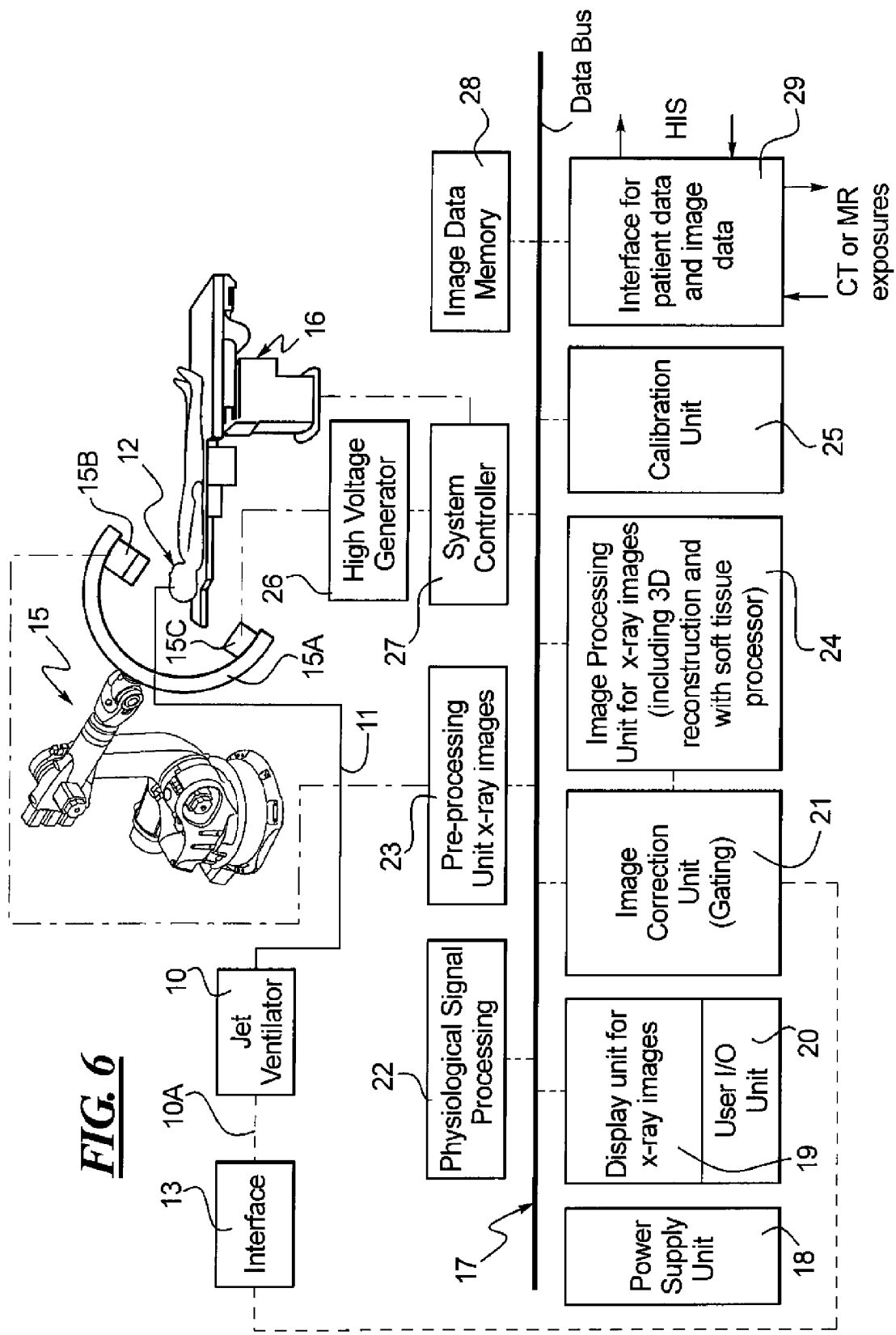
FIG. 6 is a block diagram of a first embodiment of a patient positioning table and a robotic x-ray detector system wherein a data bus with other system modules is connected with the jet ventilator via a gating image connection unit.

FIG. 6 is a first embodiment of a patient 12 on a patient table 16 using a jet ventilator 10 via ventilator output line 11 while undergoing an x-ray scan with a robotic x-ray unit 15 having C-shaped arm 15A with x-ray radiator 15B and detector 15C. Jet ventilator 10 is connected via signal output 10A through an interface 13 to an image correction unit 21 operating on the gating principle. As in FIG. 5, the patient is lying on patient table 16 and is being imaged by use of the x-ray system 15. A high voltage generator 26 connects with detector 15C and is controlled by a system controller 27 connected to the patient table 16 control input. A power supply unit 18 is also provided for the system.

As shown in FIG. 6, a common data bus 17 is provided connected to a number of units. The data bus 17 connects to a display unit for x-ray images 19 with an associated user I/O unit 20. The aforementioned image correction unit 21 also connects to the data bus 17. The same is true of a physiological signal processing unit 22 and an image processing unit for x-ray images 24 (including 3D reconstruction and with soft tissue processor).

A pre-processing unit for x-ray images unit 23 connects to the x-ray radiator 15B and also to the data bus 17.

The aforementioned system controller 27 connects to the data bus 17 along with a calibration unit 25, image data memory 28, and interface for patient data and image data 29. This interface has an input and output for CT or MR exposures and an input and output for HIS.

Figure 7:
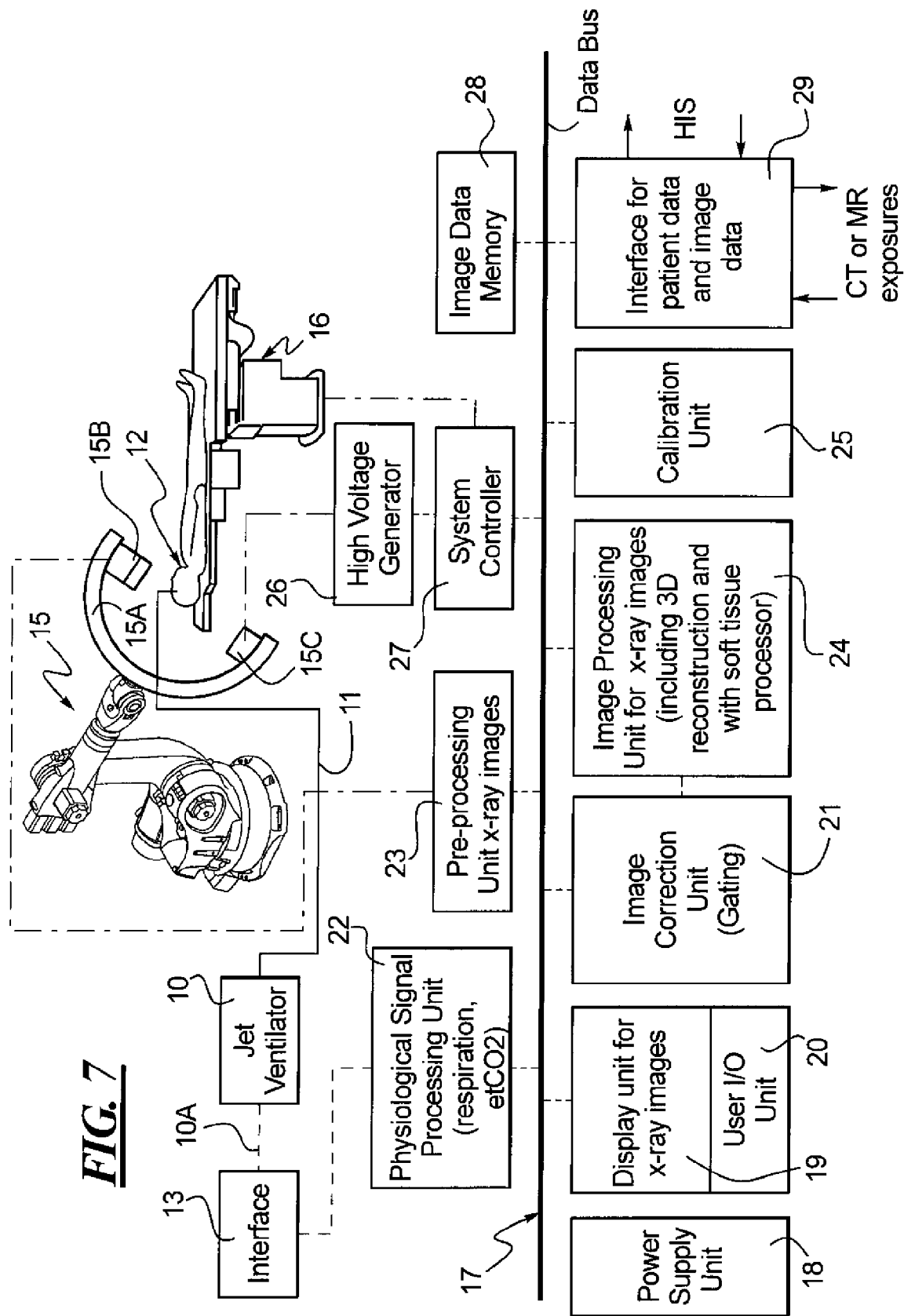
FIG. 7 is a second embodiment of a patient positioning table and robotic x-ray detector system where the jet ventilator is connected to a data line with other system modules via a physiological signal processing unit.

FIG. 7 is a second embodiment employing the jet ventilator 10 ventilating, via ventilator output line 11, a patient 12 undergoing an x-ray scan with robotic x-ray unit 15 having C-shaped arm 15A with x-ray radiator 15B and detector 15C. The jet ventilator 10 has a signal output at 10A connected through an interface 13 to a physiological signal processing unit (respiration, $CO_2$). An output of the unit 22 connects to a common data bus 17. A power supply unit 18 is also provided.

Also connected to the data bus 17 are the same units 18, 19, 20, 21, 23, 24, 25, 27, 25, 28, and 29 described for FIG. 6. A high voltage generator 26 and system controller 27 are also provided connected to the patient table 16, as was the case in FIG. 6.

While preferred embodiments have been illustrated and described in detail in the drawings and foregoing description, the same are to be considered as illustrative and not restrictive in character, it being understood that only some possible embodiments have been shown and described and that all changes and modifications that come within the spirit of the invention both now or in the future are desired to be protected.

I claim as my invention:

1. A method for minimally-invasive therapy on a patient, comprising the steps of:
   providing a minimally-invasive therapy apparatus comprising a medical tool inserted into the patient;
   providing a jet ventilator;
   while performing the minimally-invasive therapy on the patient with the minimally-invasive therapy equipment ventilating the patient with the jet ventilator to reduce a magnitude of the patient's breathing and increase a frequency of the patient's breathing; and
   synchronizing operation of the minimally-invasive therapy apparatus comprising said medical tool insertion with the jet ventilator by connecting a signal output of the jet ventilator having signals indicative of respiration breathing control to said minimally-invasive therapy equipment.

2. A method of claim 1 wherein the jet ventilator has a signal output connected to control an interface for a movement sensor and evaluation unit for movement.

3. A method of claim 2 wherein said interface connects to a data bus also connected to an image processing unit.

4. A method of claim 3 wherein the jet ventilator connects through an interface to an image correction unit.

5. A method of claim 4 wherein the image correction unit has gating controlled by a waveform of the jet ventilator.

6. A method of claim 4 wherein said image correction unit is connected to a data bus also connected to a display unit for imaging.

7. A method of claim 3 wherein a robot control unit is also connected to said data bus, said robot control unit connecting to a patient-proximal control unit for an x-ray system and a needle robot.

8. A method of claim 1 including providing an imaging device for imaging the patient to assist in performing the minimally-invasive therapy.

9. A method of claim 8 wherein said imaging device comprises an x-ray machine.

10. A method of claim 8 wherein the x-ray machine comprises a robotic x-ray detector with a C-shaped arm on which an x-ray radiator and detector are mounted.

11. A method of claim 8 wherein the ventilator has a signal output connected to an image system for at least partially controlling the image system based on ventilation by the jet ventilator.

12. A method of claim 1 wherein guidance of the medical tool is observed by use of an imaging system.

13. A method of claim 12 wherein the jet ventilator has a signal output connected through an interface to the imaging system.

14. A method of claim 1 wherein the medical tool comprises a needle inserted into the patient.

15. A method of claim 1 wherein the minimally-invasive therapy medical tool comprises a needle being inserted into a tumor in the patient.

16. A method of claim 1 wherein said jet ventilator is connected through an interface to a physiological signal processing unit.

17. A method of claim 1 wherein said physiological signal processing unit is connected to a data bus, said data bus also connecting to an image processing unit for imaging.

18. A system for minimally-invasive therapy on a patient, comprising:
   a minimally-invasive therapy apparatus comprising a medical tool inserted into the patient;
   a jet ventilator for ventilating said patient to reduce a magnitude of the patient's breathing and increase a frequency of the patient's breathing while performing the minimally-invasive therapy on the patient; and
   a control unit for said minimally-invasive therapy apparatus which receives a signal output of the jet ventilator having signals indicative of respiration breathing control to synchronize said medical tool insertion into the patient with the jet ventilator.

19. A system of claim 18 wherein further including an imaging device for imaging the patient while the minimally-invasive therapy apparatus is performing the therapy.

20. A system of claim 18 wherein the ventilator has a signal output connected to an imaging system for at least partially controlling the imaging system based on ventilation by the jet ventilator.

21. A system of claim 18 wherein the medical tool comprises a needle.

22. A system according to claim 18 wherein guidance of the medical tool is observed by use of an imaging system.

23. A system of claim 18 wherein the medical tool comprises a needle inserted into a tumor in the patient.

* * * * *